United States Patent
Govari et al.

(10) Patent No.: US 12,239,364 B2
(45) Date of Patent: Mar. 4, 2025

(54) PRINTED PROXIMAL ELECTRODES OF AN EXPANDABLE CATHETER FOR USE AS A COMMON ELECTRODE

(71) Applicant: Biosense Webster (Israel) Ltd., Yokneam (IL)

(72) Inventors: Assaf Govari, Haifa (IL); Andres Claudio Altmann, Haifa (IL); Christopher Thomas Beeckler, Brea, CA (US); Joseph Thomas Keyes, Sierra Madre, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 703 days.

(21) Appl. No.: 17/065,451

(22) Filed: Oct. 7, 2020

(65) Prior Publication Data

US 2022/0104872 A1    Apr. 7, 2022

(51) Int. Cl.
| | |
|---|---|
| *A61B 5/287* | (2021.01) |
| *A61B 5/00* | (2006.01) |
| *A61B 18/14* | (2006.01) |
| *A61B 18/00* | (2006.01) |
| *A61B 18/12* | (2006.01) |

(52) U.S. Cl.
CPC ......... *A61B 18/1492* (2013.01); *A61B 5/287* (2021.01); *A61B 5/6853* (2013.01); *A61B 5/6858* (2013.01); *A61B 2018/0022* (2013.01); *A61B 2018/00267* (2013.01); *A61B 2018/00375* (2013.01); *A61B 2018/00577* (2013.01); *A61B 2018/00958* (2013.01); *A61B 2018/126* (2013.01); *A61B 2562/0209* (2013.01)

(58) Field of Classification Search
CPC .. A61B 2018/00214; A61B 2018/0022; A61B 2018/00375; A61B 2018/386; A61B 18/16; A61B 18/162; A61B 18/165
See application file for complete search history.

(56) References Cited

U.S. PATENT DOCUMENTS

| | | |
|---|---|---|
| D123,782 S | 12/1940 | Paul |
| 3,316,896 A | 5/1967 | Louis |
| (Continued) | | |

FOREIGN PATENT DOCUMENTS

| | | |
|---|---|---|
| CN | 101422637 A | 5/2009 |
| CN | 102271607 A | 12/2011 |
| (Continued) | | |

OTHER PUBLICATIONS

European Extended Search Report dated Mar. 10, 2022, from corresponding European Application No. 21201098.7.

(Continued)

*Primary Examiner* — Eun Hwa Kim

(57) ABSTRACT

A catheter includes a shaft, an expandable frame, a first set of electrodes, and a second set of electrodes. The shaft is configured for insertion into an organ of a patient. The expandable frame is fitted at a distal end of the shaft. The first set of electrodes is disposed over a distal portion of the expandable frame, and configured to be placed in contact with a tissue in the organ. The second set of electrodes is disposed on a proximal portion of the expandable frame, and configured to be inter-connected to form a common electrode.

13 Claims, 4 Drawing Sheets

(56) References Cited

U.S. PATENT DOCUMENTS

| | | |
|---|---|---|
| 4,276,874 A | 7/1981 | Wolvek et al. |
| 4,587,975 A | 5/1986 | Salo et al. |
| 4,709,698 A | 12/1987 | Johnston et al. |
| 4,805,621 A | 2/1989 | Heinze et al. |
| 5,178,957 A | 1/1993 | Kolpe et al. |
| 5,429,617 A | 7/1995 | Hammersmark et al. |
| 5,582,609 A | 12/1996 | Swanson et al. |
| 5,584,830 A | 12/1996 | Ladd et al. |
| 5,702,386 A | 12/1997 | Stern et al. |
| 5,718,241 A | 2/1998 | Ben-Haim et al. |
| 5,797,903 A | 8/1998 | Swanson et al. |
| 5,860,974 A | 1/1999 | Abele |
| 5,971,983 A | 10/1999 | Lesh |
| 6,012,457 A | 1/2000 | Lesh |
| 6,024,740 A | 2/2000 | Lesh et al. |
| 6,042,580 A | 3/2000 | Simpson |
| 6,123,718 A | 9/2000 | Tu et al. |
| 6,164,283 A | 12/2000 | Lesh |
| 6,171,275 B1 | 1/2001 | Webster, Jr. |
| 6,176,832 B1 | 1/2001 | Habu et al. |
| 6,198,974 B1 | 3/2001 | Webster, Jr. |
| 6,226,542 B1 | 5/2001 | Reisfeld |
| 6,301,496 B1 | 10/2001 | Reisfeld |
| 6,322,558 B1 | 11/2001 | Taylor et al. |
| 6,380,957 B1 | 4/2002 | Banning |
| 6,402,740 B1 | 6/2002 | Ellis et al. |
| D462,389 S | 9/2002 | Provence et al. |
| 6,471,693 B1 | 10/2002 | Carroll et al. |
| 6,522,930 B1 | 2/2003 | Schaer et al. |
| 6,656,174 B1 | 12/2003 | Hegde et al. |
| 6,814,733 B2 | 11/2004 | Schwartz et al. |
| 6,893,433 B2 | 5/2005 | Lentz |
| 6,986,744 B1 | 1/2006 | Krivitski |
| 6,987,995 B2 | 1/2006 | Drysen |
| 6,997,924 B2 | 2/2006 | Schwartz et al. |
| 7,142,903 B2 | 11/2006 | Rodriguez et al. |
| 7,156,816 B2 | 1/2007 | Schwartz et al. |
| 7,274,957 B2 | 9/2007 | Drysen |
| 7,340,307 B2 | 3/2008 | Maguire et al. |
| 7,377,906 B2 | 5/2008 | Selkee |
| 7,442,190 B2 | 10/2008 | Abboud et al. |
| 7,536,218 B2 | 5/2009 | Govari et al. |
| 7,591,799 B2 | 9/2009 | Selkee |
| 7,593,760 B2 | 9/2009 | Rodriguez et al. |
| 7,720,517 B2 | 5/2010 | Drysen |
| 7,756,576 B2 | 7/2010 | Levin |
| 7,842,031 B2 | 11/2010 | Abboud et al. |
| 7,853,302 B2 | 12/2010 | Rodriguez et al. |
| 8,000,765 B2 | 8/2011 | Rodriguez et al. |
| 8,021,327 B2 | 9/2011 | Selkee |
| 8,048,032 B2 | 11/2011 | Root et al. |
| 8,140,170 B2 * | 3/2012 | Rezai .................. A61N 1/0558 607/116 |
| 8,231,617 B2 | 7/2012 | Satake |
| 8,267,932 B2 | 9/2012 | Baxter et al. |
| 8,275,440 B2 | 9/2012 | Rodriguez et al. |
| 8,348,888 B2 | 1/2013 | Selkee |
| 8,357,152 B2 | 1/2013 | Govari et al. |
| D682,289 S | 5/2013 | DiJulio et al. |
| D682,291 S | 5/2013 | Baek et al. |
| 8,456,182 B2 | 6/2013 | Bar-Tal et al. |
| D690,318 S | 9/2013 | Kluttz et al. |
| D694,652 S | 12/2013 | Tompkin |
| 8,641,709 B2 | 2/2014 | Sauvageau et al. |
| 8,721,590 B2 | 5/2014 | Seward et al. |
| 8,777,161 B2 | 7/2014 | Pollock et al. |
| D716,340 S | 10/2014 | Bresin et al. |
| 8,852,181 B2 | 10/2014 | Malecki et al. |
| D720,766 S | 1/2015 | Mandal et al. |
| D721,379 S | 1/2015 | Moon et al. |
| D724,618 S | 3/2015 | Shin |
| 8,998,893 B2 | 4/2015 | Avitall |
| 9,005,100 B2 | 4/2015 | Gnanashanmugam et al. |
| D729,263 S | 5/2015 | Ahn et al. |
| 9,089,350 B2 | 7/2015 | Willard |
| D736,780 S | 8/2015 | Wang |
| 9,126,023 B1 | 9/2015 | Sahatjian et al. |
| D740,308 S | 10/2015 | Kim et al. |
| D743,424 S | 11/2015 | Danielyan et al. |
| D744,000 S | 11/2015 | Mllamor et al. |
| 9,173,758 B2 | 11/2015 | Brister et al. |
| D747,742 S | 1/2016 | Fan et al. |
| D750,644 S | 3/2016 | Bhutani et al. |
| 9,283,034 B2 | 3/2016 | Katoh et al. |
| 9,289,141 B2 | 3/2016 | Lowery et al. |
| D753,690 S | 4/2016 | Vazquez et al. |
| 9,320,631 B2 | 4/2016 | Moore et al. |
| 9,345,540 B2 | 5/2016 | Mallin et al. |
| D759,673 S | 6/2016 | Looney et al. |
| D759,675 S | 6/2016 | Looney et al. |
| D764,500 S | 8/2016 | Wang |
| D765,709 S | 9/2016 | Gagnier |
| D767,616 S | 9/2016 | Jones et al. |
| D768,696 S | 10/2016 | Gagnier |
| D783,037 S | 4/2017 | Hariharan et al. |
| 9,655,677 B2 | 5/2017 | Salahieh et al. |
| D791,805 S | 7/2017 | Segars |
| 9,795,442 B2 | 10/2017 | Salahieh et al. |
| 9,907,610 B2 | 3/2018 | Beeckler et al. |
| 9,956,035 B2 | 5/2018 | Govari et al. |
| 10,201,311 B2 | 2/2019 | Chou et al. |
| D861,717 S | 10/2019 | Brekke et al. |
| 10,660,700 B2 | 5/2020 | Beeckler et al. |
| 10,688,278 B2 | 6/2020 | Beeckler et al. |
| 2001/0031961 A1 | 10/2001 | Hooven |
| 2002/0002369 A1 | 1/2002 | Hood |
| 2002/0065455 A1 | 5/2002 | Ben-Haim et al. |
| 2002/0068931 A1 | 6/2002 | Wong et al. |
| 2002/0077627 A1 | 6/2002 | Johnson et al. |
| 2002/0160134 A1 | 10/2002 | Ogushi et al. |
| 2003/0018327 A1 | 1/2003 | Truckai et al. |
| 2003/0028183 A1 | 2/2003 | Sanchez et al. |
| 2003/0050637 A1 | 3/2003 | Maguire et al. |
| 2003/0060820 A1 | 3/2003 | Maguire et al. |
| 2003/0144658 A1 | 7/2003 | Schwartz et al. |
| 2004/0122445 A1 | 6/2004 | Butler et al. |
| 2004/0147920 A1 | 7/2004 | Keidar |
| 2004/0225285 A1 | 11/2004 | Gibson |
| 2005/0070887 A1 | 3/2005 | Taimisto et al. |
| 2005/0119686 A1 | 6/2005 | Clubb |
| 2006/0013595 A1 | 1/2006 | Trezza et al. |
| 2006/0106375 A1 | 5/2006 | Werneth et al. |
| 2006/0135953 A1 | 6/2006 | Kania et al. |
| 2007/0071792 A1 | 3/2007 | Varner et al. |
| 2007/0080322 A1 | 4/2007 | Walba |
| 2007/0083194 A1 | 4/2007 | Kunis et al. |
| 2007/0129760 A1 | 6/2007 | Demarais et al. |
| 2007/0287994 A1 | 12/2007 | Patel |
| 2008/0018891 A1 | 1/2008 | Hell et al. |
| 2008/0021313 A1 | 1/2008 | Eidenschink et al. |
| 2008/0051707 A1 | 2/2008 | Phan et al. |
| 2008/0140072 A1 | 6/2008 | Stangenes et al. |
| 2008/0183132 A1 | 7/2008 | Davies et al. |
| 2008/0188912 A1 | 8/2008 | Stone et al. |
| 2008/0202637 A1 | 8/2008 | Hector et al. |
| 2008/0208186 A1 | 8/2008 | Slater |
| 2008/0249463 A1 | 10/2008 | Pappone et al. |
| 2008/0262489 A1 | 10/2008 | Steinke |
| 2008/0281312 A1 | 11/2008 | Werneth et al. |
| 2009/0036884 A1 * | 2/2009 | Gregg ................ A61B 18/1233 606/35 |
| 2009/0163890 A1 | 6/2009 | Clifford et al. |
| 2009/0182318 A1 | 7/2009 | Abboud et al. |
| 2009/0270850 A1 | 10/2009 | Zhou et al. |
| 2010/0069836 A1 | 3/2010 | Satake |
| 2010/0114269 A1 | 5/2010 | Wittenberger et al. |
| 2010/0204560 A1 | 8/2010 | Salahieh et al. |
| 2010/0256629 A1 | 10/2010 | Wylie et al. |
| 2010/0324552 A1 | 12/2010 | Kauphusman et al. |
| 2011/0118632 A1 | 5/2011 | Sinelnikov et al. |
| 2011/0130648 A1 | 6/2011 | Beeckler et al. |
| 2011/0282338 A1 | 11/2011 | Fojtik |
| 2011/0295248 A1 | 12/2011 | Wallace et al. |
| 2011/0301587 A1 | 12/2011 | Deem et al. |

(56) References Cited

U.S. PATENT DOCUMENTS

| | | |
|---|---|---|
| 2011/0313286 A1 | 12/2011 | Whayne et al. |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1 | 3/2012 | Salahieh et al. |
| 2012/0079427 A1 | 3/2012 | Carmichael et al. |
| 2012/0101413 A1 | 4/2012 | Beetel et al. |
| 2012/0101538 A1 | 4/2012 | Ballakur et al. |
| 2012/0143177 A1 | 6/2012 | Avitall |
| 2012/0143293 A1 | 6/2012 | Mauch et al. |
| 2012/0191079 A1 | 7/2012 | Moll et al. |
| 2012/0209260 A1 | 8/2012 | Lambert et al. |
| 2013/0085360 A1 | 4/2013 | Grunewald |
| 2013/0090649 A1 | 4/2013 | Smith et al. |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0318439 A1 | 11/2013 | Landis et al. |
| 2014/0012242 A1 | 1/2014 | Lee et al. |
| 2014/0018788 A1 | 1/2014 | Engelman et al. |
| 2014/0031813 A1 | 1/2014 | Tellio et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0227437 A1 | 8/2014 | DeBoer et al. |
| 2014/0243821 A1 | 8/2014 | Salahieh et al. |
| 2014/0275993 A1 | 9/2014 | Ballakur |
| 2014/0276659 A1* | 9/2014 | Juergens ............ A61B 18/1477 604/542 |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0330266 A1 | 11/2014 | Thompson et al. |
| 2014/0357956 A1 | 12/2014 | Salahieh et al. |
| 2015/0005764 A1* | 1/2015 | Hanson ............... A61B 18/1492 606/41 |
| 2015/0005799 A1 | 1/2015 | Lindquist et al. |
| 2015/0025532 A1 | 1/2015 | Hanson et al. |
| 2015/0025533 A1 | 1/2015 | Groff et al. |
| 2015/0057655 A1 | 2/2015 | Osypka |
| 2015/0067512 A1 | 3/2015 | Roswell |
| 2015/0080883 A1 | 3/2015 | Haverkost et al. |
| 2015/0105773 A1* | 4/2015 | Weber ................. A61B 5/0215 606/41 |
| 2015/0105774 A1 | 4/2015 | Lindquist et al. |
| 2015/0112256 A1 | 4/2015 | Byrne et al. |
| 2015/0112321 A1 | 4/2015 | Cadouri |
| 2015/0119875 A1 | 4/2015 | Fischell et al. |
| 2015/0141982 A1 | 5/2015 | Lee |
| 2015/0157382 A1 | 6/2015 | Avitall et al. |
| 2015/0216591 A1 | 8/2015 | Cao et al. |
| 2015/0216650 A1 | 8/2015 | Shaltis |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0272667 A1 | 10/2015 | Govari et al. |
| 2015/0327805 A1 | 11/2015 | Ben-Haim |
| 2015/0341752 A1 | 11/2015 | Flynn |
| 2016/0000499 A1 | 1/2016 | Lennox et al. |
| 2016/0051321 A1 | 2/2016 | Salahieh et al. |
| 2016/0085431 A1 | 3/2016 | Kim et al. |
| 2016/0106499 A1 | 4/2016 | Ogata et al. |
| 2016/0166306 A1 | 6/2016 | Pageard |
| 2016/0175041 A1 | 6/2016 | Govari et al. |
| 2016/0196635 A1 | 7/2016 | Cho et al. |
| 2016/0256305 A1 | 9/2016 | Longo et al. |
| 2016/0374748 A9 | 12/2016 | Salahieh et al. |
| 2017/0042614 A1 | 2/2017 | Salahieh et al. |
| 2017/0042615 A1* | 2/2017 | Salahieh .................. A61B 5/01 |
| 2017/0080192 A1 | 3/2017 | Giasolli et al. |
| 2017/0143359 A1 | 5/2017 | Nguyen et al. |
| 2017/0164464 A1 | 6/2017 | Weinkam et al. |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0347896 A1 | 12/2017 | Keyes et al. |
| 2017/0348049 A1* | 12/2017 | Vrba .................. A61B 18/1492 |
| 2018/0074693 A1 | 3/2018 | Jones et al. |
| 2018/0110562 A1 | 4/2018 | Govari et al. |
| 2018/0125575 A1 | 5/2018 | Schwartz et al. |
| 2018/0256247 A1 | 9/2018 | Govari et al. |
| 2018/0280080 A1 | 10/2018 | Govari et al. |
| 2018/0333162 A1 | 11/2018 | Saab |
| 2018/0353237 A1 | 12/2018 | Zarins et al. |
| 2018/0368927 A1 | 12/2018 | Lyons et al. |
| 2019/0059818 A1 | 2/2019 | Herrera et al. |
| 2019/0060622 A1 | 2/2019 | Beeckler |
| 2019/0143079 A1 | 5/2019 | Beeckler et al. |
| 2019/0175262 A1 | 6/2019 | Govari et al. |
| 2019/0175263 A1 | 6/2019 | Altmann et al. |
| 2019/0183567 A1 | 6/2019 | Govari et al. |
| 2019/0201669 A1 | 7/2019 | Govari et al. |
| 2019/0217065 A1 | 7/2019 | Govari et al. |
| 2019/0297441 A1 | 9/2019 | Dehe et al. |
| 2019/0298441 A1 | 10/2019 | Clark et al. |
| 2019/0365451 A1 | 12/2019 | Jung, Jr. |
| 2020/0001054 A1 | 1/2020 | Jimenez et al. |
| 2020/0015693 A1 | 1/2020 | Beeckler et al. |
| 2020/0085497 A1 | 3/2020 | Zhang et al. |
| 2020/0155226 A1 | 5/2020 | Valls et al. |
| 2021/0169567 A1 | 6/2021 | Govari et al. |
| 2021/0187254 A1 | 6/2021 | Beeckler et al. |
| 2021/0378734 A1 | 12/2021 | Govari et al. |

FOREIGN PATENT DOCUMENTS

| | | |
|---|---|---|
| CN | 102458566 A | 5/2012 |
| CN | 203539434 U | 4/2014 |
| CN | 104244856 A | 12/2014 |
| CN | 104546117 A | 4/2015 |
| CN | 105105844 A | 12/2015 |
| CN | 105473091 A | 4/2016 |
| CN | 105473093 A | 4/2016 |
| CN | 111248996 A | 6/2020 |
| EP | 0779059 A1 | 6/1997 |
| EP | 1790304 A2 | 5/2007 |
| EP | 2749214 A1 | 7/2014 |
| EP | 2865350 A2 | 4/2015 |
| EP | 2875790 A2 | 5/2015 |
| EP | 3238646 A2 | 11/2017 |
| EP | 3238648 A1 | 11/2017 |
| EP | 3251622 A1 | 12/2017 |
| EP | 3300680 A1 | 4/2018 |
| EP | 3315087 A1 | 5/2018 |
| EP | 3332727 A2 | 6/2018 |
| EP | 3571983 A2 | 11/2019 |
| EP | 3586778 A1 | 1/2020 |
| EP | 3653153 A1 | 5/2020 |
| JP | H06261951 A | 9/1994 |
| JP | H1176233 A | 3/1999 |
| JP | 2000504242 A | 4/2000 |
| JP | 2005052424 A | 3/2005 |
| JP | 2010507404 A | 3/2010 |
| JP | 2012024156 A | 2/2012 |
| JP | 2013013726 A | 1/2013 |
| JP | 2013078587 A | 5/2013 |
| JP | 2013529109 A | 7/2013 |
| JP | 2014529419 A | 11/2014 |
| JP | 2015503365 A | 2/2015 |
| JP | 2015100706 A | 6/2015 |
| JP | 2015112113 A | 6/2015 |
| JP | 2015112114 A | 6/2015 |
| JP | 2015518776 A | 7/2015 |
| JP | 2016515442 A | 5/2016 |
| JP | 2016116863 A | 6/2016 |
| WO | 0056237 A2 | 9/2000 |
| WO | 02102231 A2 | 12/2002 |

(56) References Cited

FOREIGN PATENT DOCUMENTS

| | | |
|---|---|---|
| WO | 2005041748 A2 | 5/2005 |
| WO | 2008049087 A2 | 4/2008 |
| WO | 2011143468 A2 | 11/2011 |
| WO | 2013049601 A2 | 4/2013 |
| WO | 2013052919 A2 | 4/2013 |
| WO | 2013154776 A2 | 10/2013 |
| WO | 2014168987 A1 | 10/2014 |
| WO | 2015049784 A1 | 4/2015 |
| WO | 2016183337 A2 | 11/2016 |
| WO | 2016210437 A1 | 12/2016 |
| WO | 2017024306 A1 | 2/2017 |
| WO | 2017087549 A1 | 5/2017 |
| WO | 2018106569 A1 | 6/2018 |
| WO | 2018129133 A1 | 7/2018 |
| WO | 2019095020 A1 | 5/2019 |

OTHER PUBLICATIONS

Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.

Casella M., et al., "Ablation Index as a Predictor of Long-Term Efficacy in Premature Ventricular Complex Ablation: a Regional Target Value Analysis," Heart Rhythm Society, Jun. 2019, vol. 16, No. 6, pp. 888-895.

Co-Pending U.S. Appl. No. 14/578,807, filed Dec. 22, 2014, 21 pages.

Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.

Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.

Extended European Search Report for Application No. EP17168513.4 mailed Sep. 18, 2017, 11 pages.

Extended European Search Report for European Application No. 15201723.2, mailed May 11, 2016, 07 Pages.

Extended European Search Report for European Application No. 17168393.1 mailed Dec. 15, 2017, 12 Pages.

Extended European Search Report for European Application No. 17168518.3, mailed Sep. 20, 2017, 9 Pages.

Extended European Search Report for European Application No. 17173893.3, mailed Nov. 6, 2017, 8 Pages.

Extended European Search Report for European Application No. 17201434.2, mailed Feb. 1, 2018, 10 Pages.

Extended European Search Report for European Application No. 17205876.0, mailed Jun. 1, 2018, 13 Pages.

Extended European Search Report for European Application No. 19177365.4, mailed Nov. 8, 2019, 07 Pages.

Extended European Search Report for European Application No. 19183327.6, mailed Nov. 21, 2019, 8 Pages.

Extended European Search Report for European Application No. 20153872.5, mailed May 7, 2020, 9 Pages.

Extended European Search Report for European Application No. 20195648.9, mailed Feb. 12, 2021, 8 Pages.

Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.

Haines D.E., et al., "The Promise of Pulsed Field Ablation," Dec. 2019, vol. 19, No. 12, 10 pages.

Honarbakhsh S., et al., "Radiofrequency Balloon Catheter Ablation for Paroxysmal Atrial Fibrillation, Radiance Study-a UK experience," EP Europace, Oct. 2017, vol. 19, No. 1, p. i21, 3 Pages.

International Search Report and Written Opinion for International Application No. PCT/IB2019/052313, mailed Jul. 22, 2019, 8 Pages.

International Search Report and Written Opinion for International Application No. PCT/IB2019/056381, mailed Dec. 17, 2019, 10 pages.

International Search Report and Written Opinion for International Application No. PCT/IB2019/057743, mailed Dec. 6, 2019, 16 Pages.

International Search Report and Written Opinion issued in corresponding International Application No. PCT/IB2019/057742, dated Nov. 28, 2019, 18 Pages.

Nagashima K., et al., "Hot Balloon Versus Cryoballoon Ablation for Atrial Fibrillation," Circulation: Arrhythmia and Electrophysiology, May 2018, vol. 11, No. 5, e005861, 9 Pages.

Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://www.acc.org/about-acc/press-releases/2017/03/18/08/47/sun-1045am-for-atrial-fibrillation-ablation-newer-anticoagulant-reduces-major-bleeds.

Okano T., et al., "Wire Perforation Causing Cardiopulmonary Arrest During Radiofrequency Hot Balloon Ablation for Pulmonary Vein Isolation," Journal of Cardiology Cases, Feb. 15, 2019, vol. 19, No. 5, pp. 169-172.

Partial European Search Report for European Application No. 17168393.1 mailed Sep. 13, 2017, 13 Pages.

Partial European Search Report for European Application No. 17205876.0, mailed Feb. 22, 2018, 10 Pages.

Reddy V.Y., et al., "Balloon Catheter Ablation to Treat Paroxysmal Atrial Fibrillation: What is the Level of Pulmonary Venous Isolation?," Heart Rhythm, Mar. 2008, vol. 5, No. 3, pp. 353-360, 3 Pages.

Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11, No. 6, pp. 963-968.

YOUTUBE:, "Intensity™ CX4 Professional E-Stim/ Ultrasound Combo," Dec. 22, 2015, 1 Page, [Retrieved on Nov. 19, 2020], Retrieved from URL: https://www.youtube.com/watch?v=76s1QKMWJME].

YOUTUBE: "New Interface TactiCath Contact Force Ablation Catheter," Nov. 26, 2013, 1 Pages, [Retrieved on Nov. 19, 2020], Retrieved from URL: https: /Awww.youtube.com/watch?v=aYvYO8Hpylg].

* cited by examiner

PRINTED PROXIMAL ELECTRODES OF AN EXPANDABLE CATHETER FOR USE AS A COMMON ELECTRODE

FIELD OF THE INVENTION

The present invention relates generally to invasive medical probes, and particularly to catheters comprising expandable frames for cardiac applications.

BACKGROUND OF THE INVENTION

Electrical elements disposed on a flexible printed circuit board (PCB) that is coupled to a distal end of a medical probe, were previously proposed in the patent literature. For example, U.S. Pat. No. 10,660,700 describes an irrigated balloon catheter for use in an ostium of a pulmonary vein. The balloon catheter includes a flex circuit electrode assembly adapted for circumferential contact with the ostium when the balloon is inflated. The balloon is adapted for both diagnostic and therapeutic applications and procedures. The flex circuit electrode assembly includes a substrate, a contact electrode on an outer surface of the substrate, and a wiring electrode on an inner surface of the substrate, and conductive vias extending through the substrate electrically coupling the contact electrode and the wiring electrodes. A membrane supports and carries a combined electrode and temperature sensing member which is constructed as a multi-layer flexible circuit electrode assembly.

As another example, U.S. Pat. No. 10,201,311 describes a flex-PCB catheter device that is configured to be inserted into a body lumen. The flex-PCB catheter comprises an elongate shaft, an expandable assembly, a flexible printed circuit board (flex-PCB) substrate, a plurality of electronic components and a plurality of communication paths. The elongate shaft comprises a proximal end and a distal end. The expandable assembly is configured to transition from a radially compact state to a radially expanded state. The plurality of electronic elements is coupled to the flex-PCB substrate and are configured to receive and/or transmit an electric signal. The plurality of communication paths is positioned on and/or within the flex-PCB substrate. The communication paths selectively couple the plurality of electronic elements to a plurality of electrical contacts configured to electrically connect to an electronic module configured to process the electrical signal. The flex-PCB substrate can have multiple layers, including one or more metallic layers. Acoustic matching elements and conductive traces can be included in the flex-PCB substrate.

SUMMARY OF THE INVENTION

An embodiment of the present invention that is described hereinafter provides a catheter including a shaft, an expandable frame, a first set of electrodes, and a second set of electrodes. The shaft is configured for insertion into an organ of a patient. The expandable frame is fitted at a distal end of the shaft. The first set of electrodes is disposed over a distal portion of the expandable frame, and configured to be placed in contact with a tissue in the organ. The second set of electrodes is disposed on a proximal portion of the expandable frame, and configured to be inter-connected to form a common electrode.

In some embodiments, the expandable frame is shaped to prevent the second set of electrodes from being in contact with the tissue.

In some embodiments, the expandable frame includes a membrane of an inflatable balloon. In other embodiments, the expandable frame includes spines of an expandable basket catheter.

In an embodiment, the second set of electrodes is distributed equiangularly about the longitudinal axis of the distal end.

In some embodiments, the organ is a heart, and the tissue is a pulmonary vein (PV) ostium tissue.

There is additionally provided, in accordance with another embodiment of the present invention, a system including a catheter and a switching circuitry. The catheter includes a shaft, an expandable frame, a first set of electrodes, and a second set of electrodes. The shaft is configured for insertion into an organ of a patient. The expandable frame is fitted at a distal end of the shaft. The first set of electrodes is disposed over a distal portion of the expandable frame, and configured to be placed in contact with a tissue in the organ. The second set of electrodes is disposed on a proximal portion of the expandable frame, and configured to be inter-connected to form a common electrode. The expandable frame is configured to be inter-connected to form a common electrode. The switching circuitry is configured to inter-connect at least some of the electrodes of the second set with one another to form the common electrode.

In some embodiments, the system further includes a processor configured to control the switching circuitry.

In an embodiment, the processor is configured to perform, using the switching circuitry, one or both of acquiring bipolar electrophysiological (EP) signals and applying bipolar ablation signals.

There is further provided, in accordance with another embodiment of the present invention, a method including inserting into an organ of a patient a catheter including a shaft, an expandable frame fitted at a distal end of the shaft, a first set of electrodes disposed over a distal portion of the expandable frame, and a second set of electrodes disposed on a proximal portion of the expandable frame. The first set of electrodes is placed in contact with the tissue in the organ. At least some of the electrodes of the second set are inter-connected with one another to form a common electrode. One or both of acquiring and applying signals are performed between the first set of electrodes and the common electrode.

In some embodiments, acquiring the signals includes acquiring bipolar electrophysiological (EP) signals.

In some embodiments, applying the signals includes applying bipolar ablation signals.

In an embodiment, the organ is a heart and the tissue include a pulmonary vein (PV) ostium tissue.

The present invention will be more fully understood from the following detailed description of the embodiments thereof, taken together with the drawings in which:

DETAILED DESCRIPTION OF EMBODIMENTS

Overview

Figure 1:
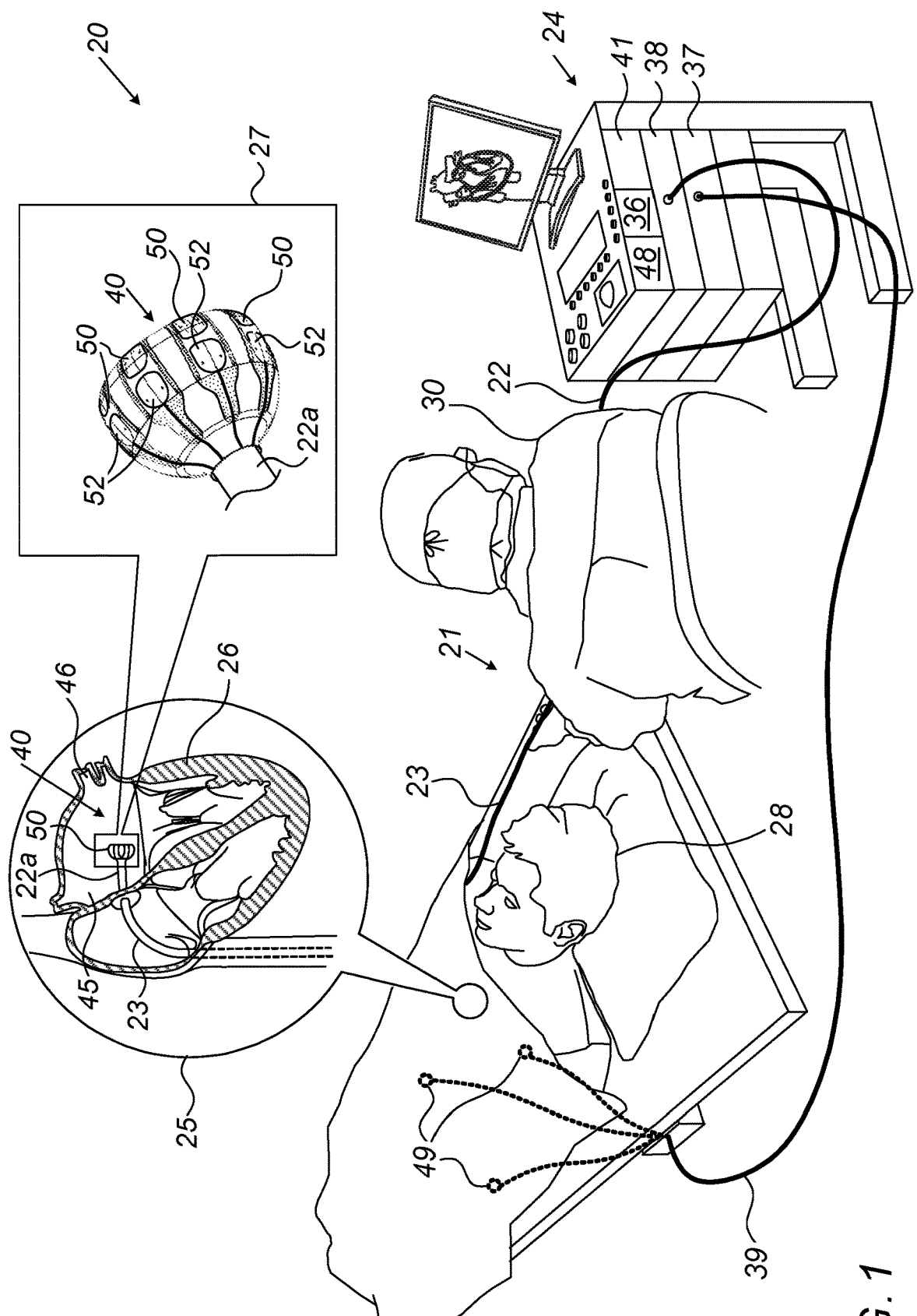
FIG. 1 is a schematic, pictorial illustration of a catheter-based cardiac diagnostics and/or therapeutic system comprising a balloon catheter, in accordance with an embodiment of the present invention.

An expandable frame (e.g., balloon or basket) fitted on a distal end of a catheter may be navigated through the cardiovascular system and inserted into a heart to perform diagnosis and/or ablation of a cardiac tissue using electrodes disposed on the frame.

The multiple electrodes can be used for tasks such as position and/or orientation tracking of the expandable frame, tissue-contact sensing, bipolar electrophysiological (EP) sensing and bipolar irreversible electroporation (IRE) and/or radiofrequency (RF) ablation.

Some of the above tasks, e.g., some forms of contact sensing, EP-sensing and IRE/RF ablation, typically make use of a "return" or "common" electrode. Such an electrode may be fitted on the catheter itself and in that case the sensing and ablation are bipolar. An additional electrode (e.g., a ring electrode) could be fitted on a distal end of a shaft of the catheter, just proximally to the expandable frame, and used as a common or return electrode. However, the need for such a ring electrode complicates the catheter, by adding manufacturing steps and special components and due to the limitations on the collapsed diameter and rigid length, a ring electrode is limited in surface area.

Embodiments of the present invention that are described hereinafter provide expandable frames with a first set of electrodes, called "distal electrodes," disposed on a distal portion of the expandable frame, and a second set of respective electrodes, called "proximal electrodes," disposed on a proximal portion of the expandable frame. The distal electrodes can be brought into contact with tissue and used for EP diagnostics and/or ablation. The proximal electrodes are located over the frame such that they are not in contact with tissue, and are jointly used as a return or common electrode.

In some embodiments, the distal and proximal sets of electrodes are arranged in electrode pairs, each pair comprising a distal and proximal electrode. The electrode pair is disposed (e.g., by being attached, plated, printed, deposited or patterned) onto a flexible printed circuit board (PCB). In an embodiment, the proximal set of electrodes is distributed equiangularly about a longitudinal axis of the distal end. For balloon catheters, each PCB is cemented to a balloon membrane. To this end, each of the flexible PCBs has an extended shape such that distal and proximal portions cover distal and proximal regions of the balloon, respectively.

In an embodiment, the proximal electrodes are all electrically interconnected to make one common proximal electrode, to, for example, replace a proximal ring electrode. In another embodiment, the proximal electrodes are selectively connected one with the other.

Typically, the proximal electrodes are interconnected using switching circuitry that can be comprised in interface circuitries, in a switching box, or in an ablation generator. In an embodiment, the proximal electrodes have permanent electrical interconnections by way of conductive links between them.

By providing a technique to realize a proximal common electrode with a flexible PCB, the cost of a one-time use multiple-electrode catheter can be significantly reduced.

System Description

FIG. 1 is a schematic, pictorial illustration of a catheter-based cardiac diagnostics and/or therapeutic system 20 comprising a balloon catheter 21, in accordance with an embodiment of the present invention. Physician 30 inserts a shaft 22 of catheter 21 through the vascular system of a patient 28 through a sheath 23. The physician then navigates a distal end 22a of shaft 22 to a target location inside a heart 26 of the patient.

Once distal end 22a of shaft 22 has reached the target location, physician 30 retracts sheath 23 and expands balloon 40, typically by pumping in saline. Physician 30 then manipulates shaft 22 such that a distal set of electrodes 50, disposed on balloon catheter 40, engage an interior wall of a PV ostium 46 in a left atrium 45, seen in inset 25. If a bipolar EP sensor detects a presence of an arrhythmogenic tissue, high-voltage bipolar IRE pulses are then applied to ostium 46.

In more detail, due to the flattened shape of the distal portion of balloon 40 (as seen in inset 27), distal electrodes 50 can be brought in contact with tissue. At the same time, the disclosed set of proximal electrodes 52 is not in contact with tissue. Some of proximal electrodes 52 are interconnected together via conductors 53, for example by using switching circuitry 36 of console 24, to form the aforementioned common electrode (e.g., for bipolar EP sensing and IRE ablation) that is immersed in blood. Alternatively, all of the proximal electrodes 52 are connected together via respective conductors 53 to the switching circuitry 36.

Certain aspects of inflatable balloons are addressed, for example, in U.S. Provisional Patent Application 62/899,259, filed Sep. 12, 2019, titled "Balloon Catheter with Force Sensor," in U.S. patent application Ser. No. 16/726,605, filed Dec. 24, 2019, titled, "Contact Force Spring with Mechanical Stops," and in U.S. patent application Ser. No. 16/892,514, filed Jun. 4, 2020, titled, "Smooth-Edge and equidistantly spaced electrodes on an expandable frame of a catheter for irreversible electroporation (IRE)," which are all assigned to the assignee of the present patent application and whose disclosures are incorporated herein by reference with a copy in the Appendix.

The proximal end of catheter 21 is connected to a console 24 comprising a processor 41, typically a general-purpose computer, with suitable front end and interface circuits 37 for receiving signals from catheter 21 and from external electrodes 49, which are typically placed around the chest of patient 26. For this purpose, processor 41 is connected to external electrodes 49 by wires running from interface circuits 37 through a cable 39.

Console 24 further comprises an IRE pulse generator configured to apply bipolar IRE pulses between electrodes 50 and interconnected proximal electrodes 52. Both sets of electrodes are connected to IRE pulse generator 38 by electrical wiring running in shaft 22 of catheter 21. A memory 48 of console 24 stores IRE protocols comprising IRE pulse parameters, such as peak voltage and pulse width.

During a procedure, system 20 can track the respective locations of electrodes 50 inside heart 26, using the Advanced Catheter Location (ACL) method, provided by Biosense-Webster (Irvine, Calif.), which is described in U.S. Pat. No. 8,456,182, whose disclosure is incorporated herein by reference.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

In particular, processor 41 runs a dedicated algorithm as disclosed herein, including FIG. 3, that enables processor 41 to perform the disclosed steps, as further described below.

In general, in the embodiment described herein, using a first set of distal electrodes 50 and a second set of proximal electrodes 52, both sets being disposed on balloon 40 of catheter 21, system 20 is capable of performing any of the aforementioned tasks of position and/or ordination tracking of balloon 40, tissue-contact sensing, bipolar electrophysiological (EP) sensing, and bipolar irreversible electroporation (IRE) and/or radiofrequency (RF) ablation, such as of PV ostium 46 tissue of heart 26.

The system of FIG. 1 is brought by way of example. Proximal electrodes 52 can therefore be interconnected by circuitries other than circuit 36. Switching elements to interconnect electrodes 52 may be realized by various electronic devices located at various places of the system, including, for example, within catheter 21.

In various embodiments, the different interface circuitry and/or switching circuitry elements of the system shown in FIG. 1 may be implemented using suitable hardware, such as using one or more discrete components (e.g., a solid-state relay) or one or more Application-Specific Integrated Circuits (ASICs).

Printed Proximal Electrodes of a Balloon Catheter

Figure 2:
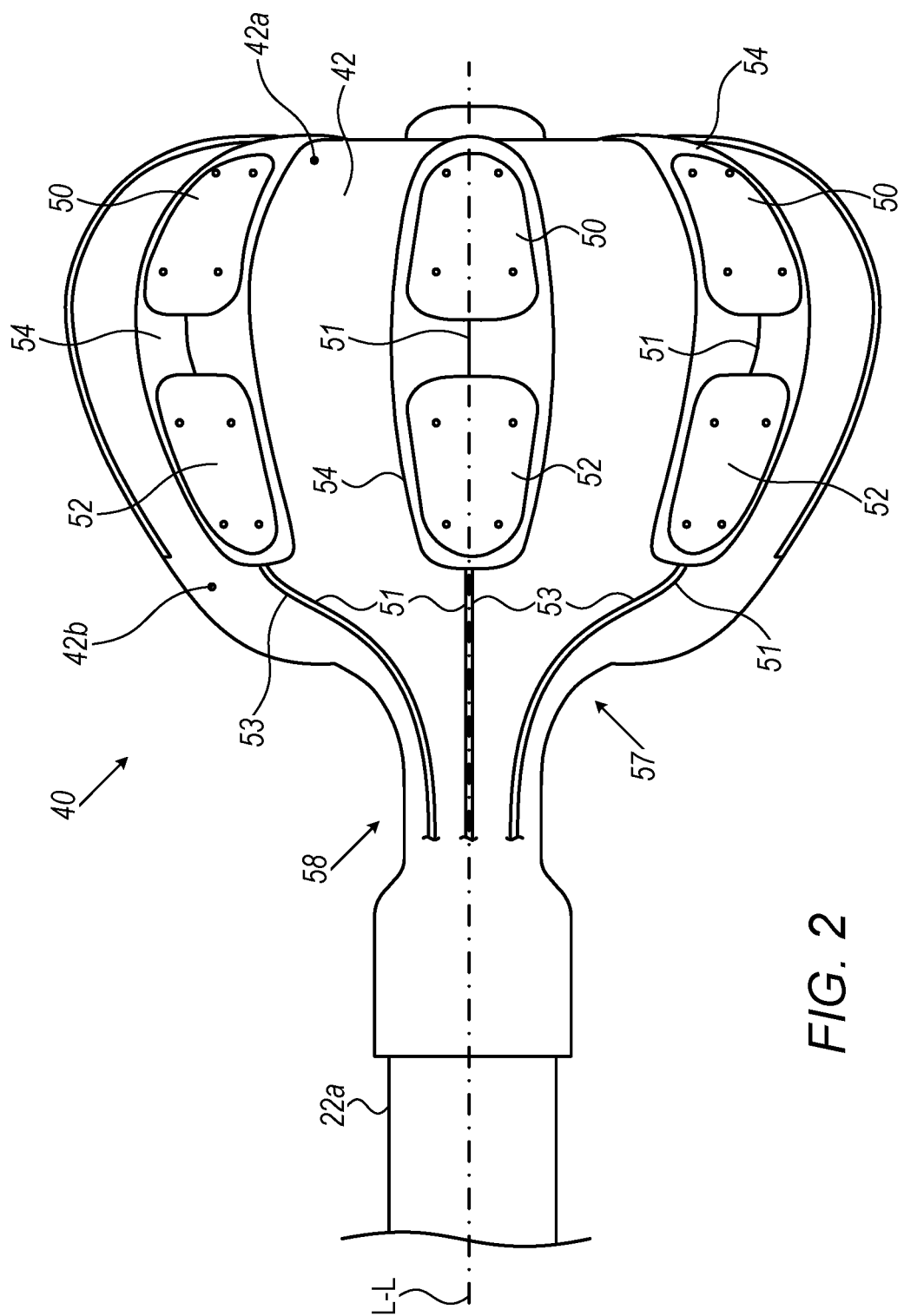
FIG. 2 is a schematic, pictorial illustration of the balloon catheter used in FIG. 1, the balloon catheter comprising distal electrodes and proximal electrodes, in accordance with an embodiment of the present invention.

FIG. 2 is a schematic, pictorial illustration of balloon catheter 40 used in FIG. 1, the balloon catheter comprising distal electrodes 50 and proximal electrodes 52, in accordance with an embodiment of the present invention. In FIG. 2, the catheter 40 extends along a longitudinal axis L-L from a proximal location (closest to an operator) to a distal location furthest away from the operator along the axis L-L. For example, portion 42a may be considered with respect to portion 42b as a "distal" portion while portion 42b may be considered a "proximal" portion.

Each pair of a distal electrode 50 and a respective proximal electrode 52 is disposed on a flexible PCB 54 that adheres to a membrane 42 of balloon 40. Each distal electrode is connected with a respective conductor 51, and each proximal electrode is connected with a respective conductor 53. Additional conductors, such as to temperature sensors, and which may together form a conductor ribbon with conductors 51/53, are not shown for clarity of presentation.

Conductors 51/53 are glued (57) at their proximal part (glue layer not shown) to the balloon and are coupled (58) to wires running inside shaft 22a (wires not shown).

In the shown embodiment, each of electrodes 50 and 52 is connected by its own conductor, for example to a respective wire running to switching circuitry 36 of system 20. To form the aforementioned common electrode, therefore, proximal electrodes 52 are interconnected by switching circuitry 36 in console 24.

Numerous elements of the balloon are omitted for clarity of presentation. Omitted elements may include, but are not limited to, (i) conductive vias extending through the substrate to electrically couple the electrodes to conductors 51 and 53, (ii) a yarn layer between membrane 42 and flexible PCB substrate 54 to lower the risk of delamination or tearing flexible PCB 54, and (iii) edge layer of flexible substrate 54, added to increase adhesion of flexible substrate 54 to membrane 42, after flexible substrate 54 is glued to membrane 43. Additional functional elements that may be disposed over balloon 40, such as temperature sensors and irrigation holes, are also omitted for clarity of presentation.

Printed Proximal Electrodes of a Basket Catheter

Figure 3:
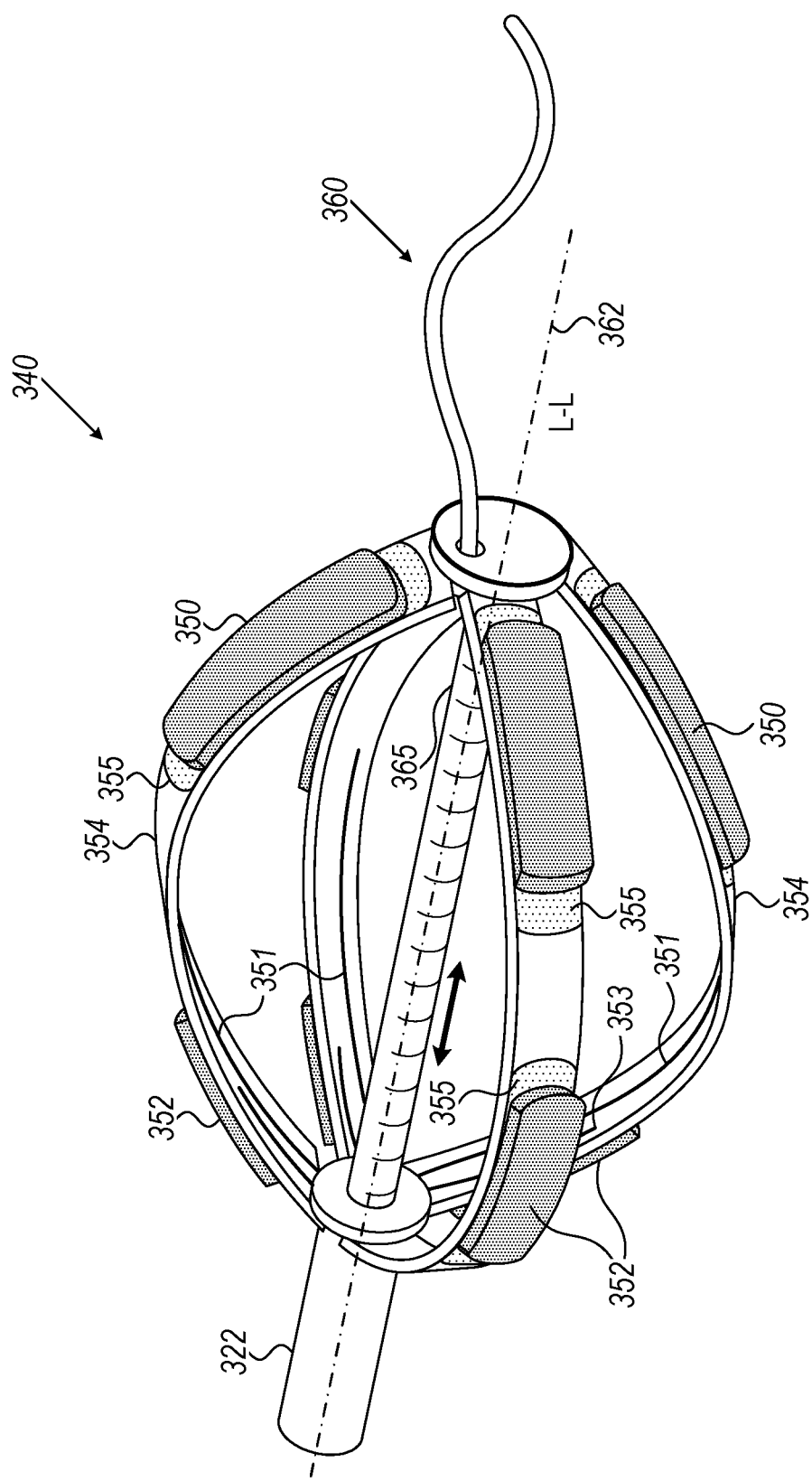
FIG. 3 is a schematic, pictorial illustration of a basket catheter that can be used with system of in FIG. 1, the basket catheter comprising distal electrodes and proximal electrodes, in accordance with an embodiment of the present invention.

FIG. 3 is a schematic, pictorial illustration of a basket catheter 340 that can be used with system 20 of in FIG. 1, the basket catheter comprising distal electrodes 350 and proximal electrodes 352, in accordance with an embodiment of the present invention.

Figure 4:
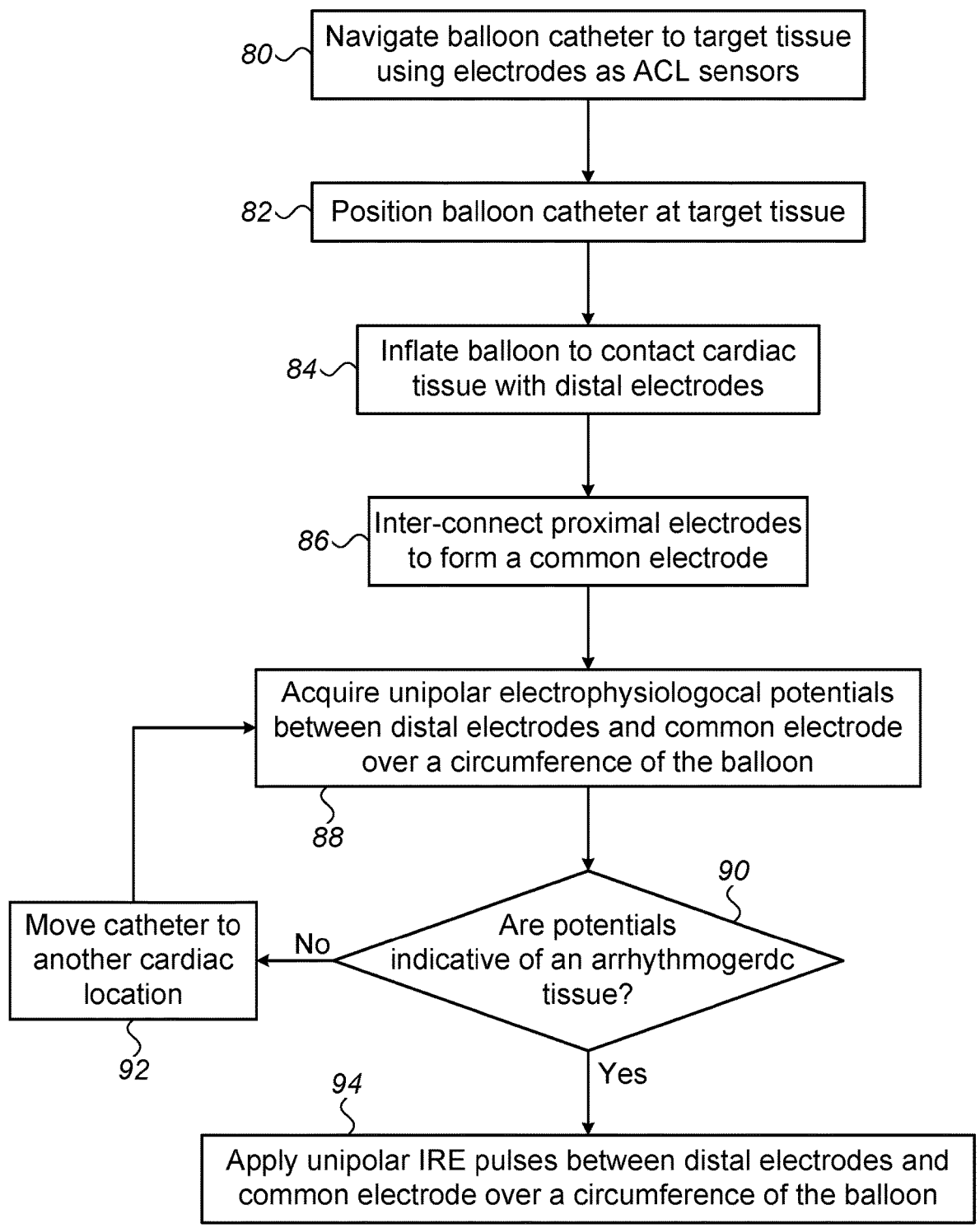
FIG. 4 is a flow chart that schematically illustrates a method for applying bipolar EP sensing and IRE pulses using the balloon catheter of FIG. 1, in accordance with an embodiment of the invention.

In FIG. 4, the catheter 340 extends along a longitudinal axis L-L 362 from a proximal location (closest to an operator) to a distal location furthest away from the operator along the axis L-L. Catheter 340 comprises a plurality of expandable spines 354 disposed about longitudinal axis 362. Distal end 365 of a shaft 322 can slide on a guidewire 360. Guidewire 360 extends through a lumen in shaft 322.

Each pair of a distal electrode 350 and a respective proximal electrode 352 is disposed on a flexible PCB 355 that that adheres to spine 354 of catheter 340. Each distal electrode is connected with a respective conductor 351, and each proximal electrode is connected with a respective conductor 353. Additional conductors, such as to temperature sensors, and which may together form a conductor ribbon with conductors 351/353, are not shown for clarity of presentation.

Conductors 351/353 are glued (glue not shown) at their proximal part to the inner side of the spines and are coupled to wires running inside shaft a 322 (wires not shown).

In the shown embodiment, each of electrodes 350 and 352 is connected by its own conductor, for example to a respective wire running to switching circuitry 36 of system 20. To form the aforementioned common electrode, therefore, proximal electrodes 352 are interconnected by switching circuitry 36 in console 24.

Numerous elements of the basket are omitted for clarity of presentation. Omitted elements may include, but are not limited to, (i) conductive vias extending through the spines to electrically couple the electrodes to conductors 351 and 353, (ii) a yarn layer between spines 354 and flexible PCB substrate 355 to lower the risk of delamination or tearing flexible PCB 355, and (iii) edge layer of flexible substrate 355, added to increase adhesion of flexible substrate 355 to spines 354, after flexible substrate 355 is glued to the spines. Additional functional elements that may be disposed over basket 340, such as temperature sensors and irrigation holes, are also omitted for clarity of presentation.

FIG. 4 is a flow chart that schematically illustrates a method for applying bipolar EP sensing and IRE pulses using balloon (40) catheter 21 of FIG. 1, in accordance with an embodiment of the invention. The algorithm, according to the presented embodiment, carries out a process that begins when physician 30 navigates the balloon catheter to a target tissue location in an organ of a patient, such as at PV ostium 46, using, for example, electrodes 50 as ACL sensing electrodes, at a balloon catheter navigation step 80.

Next, physician 30 positions the balloon catheter at ostium 46, at a balloon catheter positioning step 82. Then physician 30 fully inflates balloon 40 to contact target tissue with electrodes 50 over an entire circumference of PV ostium 46, at a balloon inflation step 84.

Next, at a switching step 86, processor 41 commands switching circuitry 36 to interconnect all proximal electrodes 52, one with the other, to form a common electrode.

At an EP diagnosis step 88, system 20 acquires bipolar EP potentials between distal electrodes 50 and the common electrode 52 over an entire circumference of balloon 40 to search for arrhythmogenic tissue.

If, at a checking step 90, analysis determines that the EP signals are normal, or at least not sufficiently indictive of an EP aberrant tissue, physician 30 moves the catheter to another cardiac location, at a catheter moving step 92, and the process returns to step 88.

If, on the other hand, at a checking step 90, analysis of the EP signals indicates an arrhythmogenic tissue, physician 30 operates system 20 to apply bipolar IRE pulses between distal electrodes 50 and the common electrode 52 to ablate tissue over the circumference of balloon 40, at an IRE ablation step 94, to isolate an arrhythmia.

Although the embodiments described herein mainly address cardiac applications, the methods and systems described herein can also be used in other medical applications, such as in neurology and Oncology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A catheter, comprising:
 a shaft for insertion into an organ of a patient;
 an expandable frame extending along a longitudinal axis from a proximal portion to a distal portion and defining a first diameter at its greatest width, the expandable frame being fitted at a distal end of the shaft and comprising a generally planar distal end;
 a plurality of flexible substrates disposed on the expandable frame, each flexible substrate extending from a proximal section to a distal section, each flexible substrate of the plurality of flexible substrates comprising a middle section having a width that is greater than a width of the proximal section or a width of the distal section;
 a first set of electrodes disposed over the distal portion of the expandable frame and configured to be placed in contact with a tissue in the organ, the distal portion of the expandable frame defining a second diameter that is less than the first diameter and spaced a first distance away from the first diameter in the distal direction, each respective electrode of the first set of electrodes disposed on the distal section of a respective flexible substrate of the plurality of flexible substrates, wherein each respective electrode of the first set of electrodes tapers from a proximal end toward a distal end of each respective electrode of the first set of electrodes and defines an apex at the distal end of each respective electrode of the first set of electrodes;
 a second set of electrodes disposed on the proximal portion of the expandable frame, the proximal portion of the expandable frame defining a third diameter spaced a second distance away from the first diameter in the proximal direction, the second distance being greater than the first distance and the second diameter being greater than the third diameter such that the expandable frame is configured to prevent the second set of electrodes from contacting the tissue in the organ, each respective electrode of the second set of electrodes disposed on the proximal section of a respective flexible substrate of the plurality of flexible substrates such that the middle section of each respective flexible substrate of the plurality of flexible substrates is positioned between a respective electrode of the first set of electrodes and a respective electrode of the second set of electrodes, wherein each electrode of the second set of electrodes tapers from a distal end toward a proximal end of each electrode of the second set of electrodes and defines an apex at the proximal end of each electrode of the second set of electrodes; and
 a switching circuit to connect at least two or more electrodes of the second set of electrodes disposed on the proximal portion to form a common electrode.

2. The catheter according to claim 1, wherein the expandable frame comprises a membrane of an inflatable balloon.

3. The catheter according to claim 1, wherein the expandable frame comprises spines of an expandable basket catheter.

4. The catheter according to claim 1, wherein the second set of electrodes is distributed equiangularly about the longitudinal axis of the expandable frame.

5. The catheter according to claim 1, wherein the organ comprises a heart and the tissue comprises a pulmonary vein (PV) ostium tissue.

6. The catheter according to claim 1, wherein the proximal section of each flexible substrate of the plurality of flexible substrates is spaced a distance away from the shaft of the catheter.

7. A system comprising:
 a catheter comprising:
 a shaft for insertion into an organ of a patient;
 an expandable frame extending along a longitudinal axis from a proximal portion to a distal portion and defining a first diameter at its greatest width, the expandable frame being fitted at a distal end of the shaft and comprising a generally planar distal end;
 a plurality of flexible substrates disposed on the expandable frame, each flexible substrate extending from a proximal section to a distal section, each flexible substrate of the plurality of flexible substrates comprising a middle section having a width that is greater than a width of the proximal section or a width of the distal section;
 a first set of electrodes disposed over the distal portion of the expandable frame and configured to be placed in contact with a tissue in the organ, the distal portion of the expandable frame defining a second diameter that is less than the first diameter and spaced a first distance away from the first diameter in the distal direction, each respective electrode of the first set of electrodes disposed on the distal section of a respective flexible substrate of the plurality of flexible substrates, wherein each respective electrode of the first set of electrodes tapers from a proximal end toward a distal end of each respective electrode of the first set of electrodes and defines an apex at the distal end of each respective electrode of the first set of electrodes;

a second set of electrodes disposed on the proximal portion of the expandable frame, the proximal portion of the expandable frame defining a third diameter spaced a second distance away from the first diameter, the second distance being greater than the first distance and the second diameter being greater than the third diameter such that the expandable frame is configured to prevent the second set of electrodes from contacting the tissue in the organ, each respective electrode of the second set of electrodes disposed on the proximal section of a respective flexible substrate of the plurality of flexible substrates such that the middle section of each respective flexible substrate of the plurality of flexible substrates is positioned between a respective electrode of the first set of electrodes and a respective electrode of the second set of electrodes, wherein each electrode of the second set of electrodes tapers from a distal end toward a proximal end of each electrode of the second set of electrodes and defines an apex at the proximal end of each electrode of the second set of electrodes; and a switching circuitry that inter-connects at least some of the electrodes of the second set with one another to form the common electrode.

8. The system according to claim 7, and comprising a processor configured to control the switching circuitry.

9. The system according to claim 8, wherein the processor is configured to perform, using the switching circuitry, one or both of acquiring bipolar electrophysiological (EP) signals and applying bipolar ablation signals.

10. A method comprising:

inserting into an organ of a patient a catheter, comprising:

a shaft;

an expandable frame fitted at a distal end of the shaft and comprising a generally planar distal end, the expandable frame extending along a longitudinal axis from a proximal portion to a distal portion and defining a first diameter at its greatest width;

a plurality of flexible substrates disposed on the expandable frame, each flexible substrate comprising a proximal section and a distal section, each flexible substrate of the plurality of flexible substrates comprising a middle section having a width that is greater than a width of the proximal section or a width of the distal section;

a first set of electrodes disposed over the distal portion of the expandable frame and configured to be placed in contact with a tissue in the organ, the distal portion of the expandable frame defining a second diameter that is less than the first diameter and spaced a first distance away from the first diameter in the distal direction, each respective electrode of the first set of electrodes disposed on the distal section of a respective flexible substrate of the plurality of flexible substrates, wherein each respective electrode of the first set of electrodes tapers from a proximal end toward a distal end of each respective electrode of the first set of electrodes and defines an apex at the distal end of each respective electrode of the first set of electrodes;

a second set of electrodes disposed on the proximal portion of the expandable frame, the proximal portion of the expandable frame defining a third diameter spaced a second distance away from the first diameter, the second distance being greater than the first distance and the second diameter being greater than the third diameter such that the expandable frame is configured to prevent the second set of electrodes from contacting the tissue in the organ, each respective electrode of the second set of electrodes disposed on the proximal section of a respective flexible substrate of the plurality of flexible substrates such that the middle section of each respective flexible substrate of the plurality of flexible substrates is positioned between a respective electrode of the first set of electrodes and a respective electrode of the second set of electrodes, wherein each electrode of the second set of electrodes tapers from a distal end toward a proximal end of each electrode of the second set of electrodes and defines an apex at the proximal end of each electrode of the second set of electrodes;

placing the first set of electrodes in contact with the tissue in the organ;

inter-connecting at least some of the electrodes of the second set with one another to form a common electrode; and performing one or both of acquiring and applying signals between the first set of electrodes and the common electrode.

11. The method according to claim 10, wherein acquiring the signals comprises acquiring bipolar electrophysiological (EP) signals.

12. The method according to claim 10, wherein applying the signals comprises applying bipolar ablation signals.

13. The method according to claim 10, wherein the organ comprises a heart and the tissue comprises a pulmonary vein (PV) ostium tissue.

* * * * *